United States Patent
Takeuchi et al.

[11] Patent Number: 5,929,115
[45] Date of Patent: Jul. 27, 1999

[54] ANTI-INFLAMMATORY EYE DROP

[75] Inventors: Masanobu Takeuchi; Hiroki Maruyama; Hiroe Suzuki; Touru Oguma; Makoto Maeda, all of Tokyo, Japan

[73] Assignee: Wakamoto Pharmaceutical Co., Ltd., Tokyo, Japan

[21] Appl. No.: 08/875,101

[22] PCT Filed: Dec. 26, 1995

[86] PCT No.: PCT/JP95/02680

§ 371 Date: Jul. 21, 1997

§ 102(e) Date: Jul. 21, 1997

[87] PCT Pub. No.: WO96/22088

PCT Pub. Date: Jul. 25, 1996

[30] Foreign Application Priority Data

Jan. 20, 1995 [JP] Japan ................................ 7-24485

[51] Int. Cl.$^6$ ................................................. A61K 31/195
[52] U.S. Cl. ............................................ 514/567; 514/912
[58] Field of Search ........................................ 514/567, 912

[56] References Cited

U.S. PATENT DOCUMENTS

| | | | |
|---|---|---|---|
| 4,829,088 | 5/1989 | Doulakas | 514/567 |
| 4,960,799 | 10/1990 | Nagy et al. | |
| 5,576,311 | 11/1996 | Guy | 514/179 |

FOREIGN PATENT DOCUMENTS

| | | |
|---|---|---|
| 0 306 984 | 3/1989 | European Pat. Off. |
| 0 472 327 | 2/1992 | European Pat. Off. |
| 0 592 348 | 4/1994 | European Pat. Off. |
| 36 12 537 | 7/1987 | Germany |
| 94/10976 | 5/1994 | WIPO |

OTHER PUBLICATIONS

Database WPI, Derwent Publications, AN 83–823242, JP 58–174309, Oct. 13, 1983.
Database WPI, Derwent Publications, AN 83–823243, JP 58–174310, Oct. 13, 1983.
Database WPI, Derwent Publications, AN 84–078369, JP 59–029616, Feb. 16, 1984.
Database WPI, Derwent Publications, AN 85–213741, JP 60–136516, Jul. 20, 1985.

*Primary Examiner*—Zohreh Fay
*Attorney, Agent, or Firm*—Oblon, Spivak, McClelland, Maier & Neustadt, P.C.

[57] ABSTRACT

An anti-inflammatory eye drop comprises
 (a) 0.05 to 0.7 weight/volume % of diclofenac sodium;
 (b) 1 to 10 weight/volume % of γ-cyclodextrin;
 (c) 1 to 20 weight/volume % of polyvinyl pyrrolidone; and
 (d) 0.002 to 0.01 weight/volume % of benzethonium chloride or 0.002 to 0.005 weight/volume % of benzalkonium chloride,
and has a pH value ranging from 7.0 to 8.5.

The anti-inflammatory eye drop may comprise diclofenac sodium in a wide range of concentration, is stable over a long time period and shows only a low degree of ocular irritation.

12 Claims, No Drawings

ANTI-INFLAMMATORY EYE DROP

This application is a 371 of PCT/JP95/02680 filed Dec. 26, 1995.

TECHNICAL FIELD

The present invention relates to an anti-inflammatory eye drop comprising diclofenac sodium (hereinafter referred to as DFNa) as an effective component, to which γ-cyclodextrin (hereinafter referred to as γ-CyD) which is a water-soluble cyclodextrin and a polyvinylpyrrolidone (hereinafter referred to as PVP) are added to impart storage stability over a long period of time to the eye drop and to alleviate ocular irritation thereof.

BACKGROUND ART

An aqueous eye drop comprising DFNa which is a non-steroidal anti-inflammatory agent has been used for protecting a patient from suffering from post-operative inflammatory conditions and complications during and after operations, when the patient is subjected to cataract surgery, because of the strong prostaglandin biosynthesis-inhibitory action of the anti-inflammatory agent. If the non-steroidal anti-inflammatory agents are used in eye drops, most of these anti-inflammatory agents have an irritating action to mucous membranes and eyes and an effect of causing a strong ocular pain.

The inventors of this invention have provided an anti-inflammatory eye drop which comprises at least one non-steroidal anti-inflammatory agents selected from the group consisting of ibuprofen, indometacin, ketoprofen, naproxen and flufenamic acid as a basis and a salt of calcium or magnesium with a physiologically acceptable acid as an ocular irritation-alleviating agent [Japanese Examined Patent Publication (hereinafter referred to as "J.P. KOKOKU) No. Hei 1-19362] in order to alleviate the ocular irritation and the ocular pain induced by the non-steroidal anti-inflammatory agent. In addition, the inventors have provided an anti-inflammatory eye drop which comprises DFNa and polyoxyethylene sorbitan monooleate or α- and β-cyclodextrin, as an auxiliary agent for dissolution, in an amount ranging from 5 to 10 times (weight basis) the amount of DFNa (J.P. KOKOKU No. Hei 2-6329). Moreover, the inventors of this invention have developed an eye drop which comprises a chemically modified β-cyclodextrin in combination with DFNa and which does not cause ocular irritation immediately after being dropped in the eyes and is excellent in storage stability and filed a patent application [Japanese Un-Examined Patent Publication (hereinafter referred to as "J.P. KOKAI") No. Hei 6-16547].

Furthermore, there has been proposed a therapeutic agent comprising an aqueous solution which contains DFNa as an effective component, a buffering agent, an auxiliary agent for dissolution and a preservative and which further comprises 2-amino-2-hydroxymethyl-1,3-propanediol or a homologue thereof having up to 10 carbon atoms as a stabilizer for the effective component and the preservative (J.P. XOKAI No. Sho 62-242617). On the other hand, there have been proposed, as cyclodextrin-containing eye drops, an anti-inflammatory ophthalmic solution which comprises 2-(2-fluoro-4-biphenylyl)propionic acid or a salt thereof and β-cyclodextrin (hereinafter referred to as "β-CyD") or γ-CyD (J.P. KOKOKU No. Hei 3-30571); an anti-inflammatory ophthalmic solution which comprises 2-(2-fluoro-4-biphenylyl)propionic acid or a salt thereof, β-CyD or γ-CyD and a calcium salt or a magnesium salt (J.P. KOKAI No. Sho 60-136516); or an aqueous ophthalmic solution which comprises 3,4-dihydro-2,8-diisopropyl-3-thioxo-2H-1,4-benzoxadine-4-acetic acid or a salt thereof as a basis and cyclodextrin (J.P. KOKAI No. Hei 5-213757).

The calcium or magnesium salt of a physiologically acceptable acid shows a satisfactory effect of alleviating the ocular irritation of the resulting eye drop, but the eye drop containing the same suffers from a problem such that it is insufficient in the long term storage stability. The α-cyclodextrin as disclosed in J.P. KOKOKU No. Hei 2-6329 does not have any effect of alleviating the ocular irritation due to DFNa, while β-CyD shows a weak ocular irritation-alleviating effect, but the effect is insufficient. Thereafter the inventors of this invention have found out that the incorporation of a chemically modified water-soluble β-CyD into such an eye drop containing DFNa in an amount of 7 to 50 times the amount of the latter results in the formation of an eye drop having excellent ocular irritation-alleviating effect and excellent storage stability (J.P. KOKAI No. Hei 6-16547). However, the incorporation thereof does not ensure a sufficient ocular irritation-alleviating effect at a DFNa concentration of higher than 0.1%. The eye drop exemplified in J.P. KOKAI No. Sho 62-242617 shows considerably high storage stability, but strongly irritates the eyes immediately after it is dropped in the eyes and therefore, these conventional eye drops have not yet been satisfied.

Moreover, J.P. KOKAI Nos. Sho 60-136516 and Hei 5-213757 which are improved inventions of that disclosed in the foregoing J.P. KOKOKU No Hei 3-30571 disclose that β-CyD and γ-CyD have an effect of alleviating the ocular irritation caused by the effective component, but γ-CyD does not show a sufficient effect in the both cases.

On the other hand, γ-CyD has been known to show local safety identical to or higher than that observed for the chemically modified water-soluble β-CyD (Uekama, Pharm. Tech. Japan, 1991, 7(2), p. 143). It has conventionally been difficult to mass-produce γ-CyD and the price thereof is very high, i.e., about 100 times that of β-CyD. Therefore, γ-CyD has not been used at all from the economical standpoint. However, there has recently been developed a new technique for manufacturing the same, it has been put on the market at a low price and has attracted special interest recently as an additive for drugs.

DISCLOSURE OF THE INVENTION

Under such circumstances, the inventors have conducted various studies to develop an eye drop comprising DFNa as a basis, which does not cause any ocular irritation immediately after being dropped in the eyes, has long term storage stability and can be used in a wide range of the DFNa concentration, through the use of γ-CyD, and as a result, have found out that the foregoing object can be achieved by using a combination of DFNa, γ-CyD, PVP and benzethonium chloride or benzalkonium chloride as a preservative and by adjusting the pH value to the range of from 7.0 to 8.5, and thus have completed the present invention. In other words, the present invention relates to an anti-inflammatory eye drop which comprises DFNa, γ-CyD, PVP and benzethonium chloride or benzalkonium chloride and whose pH value ranges from 7.0 to 8.5.

The stimulation of DFNa to the human eyes is in general intensified when the DFNa concentration is not less than 0.05%. The inventors of this invention have surprisingly found out such new knowledges that the stimulation of DFNa to the human eyes can considerably be alleviated and DFNa can be used in a high concentration which permits the achievement of a sufficient therapeutic effect depending on the conditions of a variety of eye diseases, by the use of γ-CyD simultaneously with DFNa and by adjusting the pH value to a level ranging from 7.0 to 8.5, and that the eye drop having long term storage stability can be obtained by the use of PVP and benzethonium chloride or benzalkonium chloride as a preservative simultaneously with DFNa and the inventors have thus completed the present invention.

Conventionally, the concentration of DFNa usable in the eye drop product has been limited to a level of up to 0.1% because of the strong irritation action to the eyes. In the eye drop of the present invention, however, the ocular irritation of DFNa is substantially alleviated and DFNa can be used in the eye drop product in a high concentration on the order of up to 0.7%, by the simultaneous use of γ-CyD in an amount ranging from 1 to 10% and by adjusting the pH value to a level ranging from 7.0 to 8.5. For this reason, the resulting eye drop can be used in wide variety of fields.

A high concentration of DFNa more conspicuously shows an intra-ocular prostaglandin-inhibitory effect and an atropine-induced mydriatic effect and therefore, not only shows marked effect in the maintenance of mydriasis and anti-inflammation during ocular surgery (of, for instance, cataract, glaucoma, retinal detachment, removal of vitreous body and strabismus), or in the therapeutic treatment after operations, but also shows effect of treating general eye diseases, i.e., various symptoms in which prostaglandin is involved, for instance, Behcet's disease, endogenous uveitis and inflammatory disease of outer ocular area (such as conjunctivitis, keratitis, episcleritis, pinguecula and hordeolum).

BEST MODE FOR CARRYING OUT THE INVENTION

The γ-CyD used in the present invention can alleviate the ocular irritation caused by DFNa over a wide concentration range extending from a low concentration to a high concentration. The effectiveness over such a wide concentration range is peculiar to γ-CyD, while other water-soluble cyclodextrins never show such an excellent effect at all.

The PVP used in the present invention prevents any generation of insoluble matter originated from γ-CyD present in the formulation. J.P. KOKAI No. Hei 5-213757 discloses the insoluble matter generation-inhibitory effect of PVP and other water-soluble polymers such as polyvinyl alcohol, hydroxyethyl cellulose, methyl cellulose, hydroxypropylmethyl cellulose, sodium alginate, sodium carboxymethyl cellullose and polyethylene glycol, but the inventors of this invention have carried out the supplementary examination of this technique and have found out that the water-soluble polymers other than PVP do not exhibit such an effect at all and that the effect is peculiar to PVP.

The PVP used in the present invention preferably has a Fikentscher's K-value ranging from 10 to 95. Such PVP are sold by BASF Japan Co., Ltd. under the trade name of Kollidone™ 12PF, Kollidone™ 17PF, Kollidone™ 25, Kollidone™ 30 and Kollidone™ 90; and by Tokyo Chemical Industry Co., Ltd. under the trade name of PVP K15, PVP K30, PVP K60 and PVP K90, which are all easily available.

The preservatives used in the present invention is exclusively selected from benzethonium chloride or benzalkonium chloride for the purpose of providing an eye drop having long term storage stability. More specifically, the experiments of the inventors indicate that benzethonium chloride or benzalkonium chloride has quite characteristic properties as shown in Table 3 given below and shows a foreign substance generation-inhibitory effect considerably higher than that observed for other preservatives.

The eye drop of the present invention is prepared by adding DNFa and γ-CyD to purified water to thus dissolve the same, then adding PVP and benzethonium chloride or benzalkonium chloride to the resulting solution and adjusting the pH value to the range of from 7.0 to 8.5 using a buffering agent and a pH adjustor.

The concentration of DFNa in the final composition of the present invention ranges from 0.05 to 0.7 w/v% (hereunder the unit "w/v %" will be referred to as "%" for simplicity) and particularly preferably 0.1 to 0.5%. If the concentration of DFNa is less than 0.05%, the eye drop is not practical because of low anti-inflammatory therapeutic effect, while if it exceeds 0.7%, it becomes difficult to prepare such an eye drop composition.

The concentration of γ-CyD in the final composition of the present invention ranges from 1 to 10% and particularly preferably 3 to 10%. When the DFNa concentration falls within the range defined above, the use of the γ-CyD concentration lower than 1% does not ensure the achievement of the intended effect of alleviating ocular irritation and the use thereof in an amount of more than 10% is not preferred from the economical standpoint and from the viewpoint of the ability of a drug to be formed into pharmaceutical preparation.

The PVP concentration in the final composition according to the present invention ranges from 1 to 20% and particularly preferably 2 to 10%. If the PVP concentration is less than 1%, insoluble matter is formed and the resulting composition is insufficient in the storage stability, while if it exceeds 20%, the resulting composition gives an increased sticky-feeling to patients when it is dropped in the eyes.

The pH value of the eye drop of the present invention ranges from 7.0 to 8.5 and particularly preferably 7.5 to 8.5. If the pH value is less than 6.5, the intended effect of alleviating ocular irritation cannot be achieved even if the γ-CyD concentration is controlled so as to fall within the range of from 5 to 10%. On the other hand, the use of the pH value of higher than 8.5 is not preferred since the pH value is beyond the physiological pH range. The pH value may be controlled by the use of a buffering agent such as a borate buffer or a phosphate buffer or a pH adjustor such as an aqueous solution of sodium hydroxide or dilute hydrochloric acid according to the usual manner, but the present invention is not restricted to these specific control means.

Benzethonium chloride or benzalkonium chloride used in the present invention has a bactericidal action which can prevent any contamination of the eye drop with microorganisms during using the same. The concentration preferably ranges from 0.002 to 0.01% for benzethonium chloride. If the benzethonium chloride concentration is less than 0.002%, the bactericidal action of the resulting eye drop is not sufficient, while if it exceeds 0.01%, the eye drop may cause corneal epithelial damage when the eye drop is frequently used. On the other hand, the concentration of benzalkonium chloride preferably ranges from 0.002 to 0.005%. If the benzalkonium chloride concentration is less than 0.002%, the bactericidal action is insufficient, while if it exceeds 0.005%, the resulting composition becomes turbid and thus the eye drop of the present invention cannot be prepared.

The eye drop of the present invention may comprise other components usually used in eye drops in addition to the foregoing components insofar as the object of the present invention is not impaired. Such other additives include, for instance, a buffering agent, an isotonicity, a surfactant and a chelating agent. Examples of buffering agents are phosphoric acid salts, boric acid salts and organic bases. Examples of isotonicities include sodium chloride, potassium chloride, boric acid and sodium borate. Examples of surfactants are polysorbate 80 and polyoxyethylene-hydrogenated castor oil 60. In addition, examples of chelating agents are sodium edetate and sodium citrate.

The present invention will further be described in more detail with reference to the following Experiments and examples of formulations, but the present invention is not restricted to these specific examples.

EXAMPLE 1

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| PVP$_{K30}$ (Kollidon ™ 30: available from BASF Japan Co., Ltd.) | 2.0 g |
| benzethonium chloride | 0.005 g |
| 0.1N HCl/0.1N NaOH amount sufficient for achieving | pH 8.0 |
| purified water | ad. 100 ml |

To 80 ml of purified water, there are added diclofenac sodium, γ-CyD, boric acid, sodium borate, PVP$_{K30}$ and benzethonium chloride to dissolve them in the water. The pH of the resulting solution is adjusted to 8.0 by addition of 0.1N HCl or 0.1N NaOH, then purified water is added till the total volume reaches 100 ml, followed by sterilization through filtration to give an eye drop.

EXAMPLE 2

| | |
|---|---|
| diclofenac sodium | 0.05 g |
| γ-CyD (available from Wacker Chemicals East Asia Co., Ltd.) | 10.0 g |
| boric acid | 1.60 g |
| sodium borate | 0.16 g |
| PVP$_{K25}$ (Kollidon ™ 25: available from BASF Japan Co., Ltd.) | 10.0 g |
| benzethonium chloride | 0.005 g |
| 0.1N HCl/0.1N NaOH amount sufficient for achieving | pH 7.0 |
| purified water | ad. 100 ml |

The same procedures used in Example 1 were repeated except that the foregoing formulation is substituted for that used in Example 1 to give an eye drop.

EXAMPLE 3

| | |
|---|---|
| diclofenac sodium | 0.05 g |
| γ-CyD (available from Wacker Chemicals East Asia Co., Ltd.) | 1.0 g |
| boric acid | 1.10 g |
| sodium borate | 2.10 g |
| PVP$_{K90}$ (Kollidon ™ 90: available from BASF Japan Co., Ltd.) | 1.0 g |
| benzethonium chloride | 0.005 g |
| 0.1N HCl/0.1N NaOH amount sufficient for achieving | pH 8.5 |
| purified water | ad. 100 ml |

The same procedures used in Example 1 were repeated except that the foregoing formulation is substituted for that used in Example 1 to give an eye drop.

EXAMPLE 4

| | |
|---|---|
| diclofenac sodium | 0.1 g |
| γ-CyD (available from Wacker Chemicals East Asia Co., Ltd.) | 3.0 g |
| boric acid | 1.10 g |
| sodium borate | 2.10 g |
| PVP$_{K25}$ (Kollidon ™ 25: available from BASF Japan Co., Ltd.) | 5.0 g |
| benzalkonium chloride | 0.005 g |
| 0.1N HCl/0.1N NaOH amount sufficient for achieving | pH 8.5 |
| purified water | ad. 100 ml |

The same procedures used in Example 1 were repeated except that the foregoing formulation is substituted for that used in Example 1 to give an eye drop.

EXAMPLE 5

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| PVP$_{K25}$ (Kollidon ™ 25: available from BASF Japan Co., Ltd.) | 3.0 g |
| benzalkonium chloride | 0.002 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

EXAMPLE 6

| | |
|---|---|
| diclofenac sodium | 0.5 g |
| γ-CyD (available from Wacker Chemicals East Asia Co., Ltd.) | 10.0 g |
| boric acid | 1.10 g |
| sodium borate | 2.10 g |
| PVP$_{K25}$ (Kollidon ™ 25: available from BASF Japan Co., Ltd.) | 10.0 g |
| benzethonium chloride | 0.005 g |
| 0.1N HCl/0.1N NaOH amount sufficient for achieving | pH 8.5 |
| purified water | ad. 100 ml |

The same procedures used in Example 1 were repeated except that the foregoing formulation is substituted for that used in Example 1 to give an eye drop.

EXAMPLE 7

| | |
|---|---|
| diclofenac sodium | 0.7 g |
| γ-CyD (available from Wacker Chemicals East Asia Co., Ltd.) | 10.0 g |
| boric acid | 1.10 g |
| sodium borate | 2.10 g |
| PVP$_{K25}$ (Kollidon ™ 25: available from BASF Japan Co., Ltd.) | 10.0 g |
| benzethonium chloride | 0.01 g |
| 0.1N HCl/0.1N NaOH amount sufficient for achieving | pH 8.5 |
| purified water | ad. 100 ml |

The same procedures used in Example 1 were repeated except that the foregoing formulation is substituted for that used in Example 1 to give an eye drop.

EXAMPLE 8

| | |
|---|---|
| diclofenac sodium | 0.1 g |
| γ-CyD (available from Wacker Chemicals East Asia Co., Ltd.) | 3.0 g |
| boric acid | 1.45 g |
| sodium borate | 0.35 g |
| $PVP_{K25}$ (Kollidon ™ 25: available from BASF Japan Co., Ltd.) | 10.0 g |
| benzethonium chloride | 0.002 g |
| 0.1N HCl/0.1N NaOH amount sufficient for achieving | pH 7.5 |
| purified water | ad. 100 ml |

The same procedures used in Example 1 were repeated except that the foregoing formulation is substituted for that used in Example 1 to give an eye drop.

EXAMPLE 9

| | |
|---|---|
| diclofenac sodium | 0.05 g |
| γ-CyD (available from Wacker Chemicals East Asia Co., Ltd.) | 10.0 g |
| boric acid | 1.10 g |
| sodium borate | 2.10 g |
| $PVP_{K12}$ (Kollidon ™ 12PF: available from BASF Japan Co., Ltd.) | 20.0 g |
| benzethonium chloride | 0.002 g |
| 0.1N HCl/0.1N NaOH amount sufficient for achieving | pH 8.5 |
| purified water | ad. 100 ml |

The same procedures used in Example 1 were repeated except that the foregoing formulation is substituted for that used in Example 1 to give an eye drop.

EXAMPLE 10

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| $PVP_{K90}$ (Kollidon ™ 90: available from BASF Japan Co., Ltd.) | 1.0 g |
| benzethonium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| $PVP_{K25}$ (Kollidon ™ 25: available from BASF Japan Co., Ltd.) | 3.0 g |
| benzethonium chloride | 0.005 g |
| 0.1N HCl/0.1N NaOH amount sufficient for achieving | pH 8.0 |
| purified water | ad. 100 ml |

EXAMPLE 11

The same procedures used in Example 1 were repeated except that the foregoing formulation is substituted for that used in Example 1 to give an eye drop.

EXAMPLE 12

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| $PVP_{K25}$ (Kollidon ™ 25: available from BASF Japan Co., Ltd.) | 5.0 g |
| benzethonium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

EXAMPLE 13

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| $PVP_{K25}$ (Kollidon ™ 25: available from BASF Japan Co., Ltd.) | 7.0 g |
| benzethonium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

EXAMPLE 14

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| $PVP_{K25}$ (Kollidon ™ 25: available from BASF Japan Co., Ltd.) | 10.0 g |
| benzethonium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

EXAMPLE 15

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| $PVP_{K17}$ (Kollidon ™ 17PF: available from BASF Japan Co., Ltd.) | 12.0 g |
| benzethonium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

EXAMPLE 16

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| PVP $_{K15}$ (available from Tokyo Chemical Industry Co., Ltd.) | 15.0 g |
| benzethonium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

EXAMPLE 17

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| PVP $_{K12}$ (Kollidon ™ 12PF: available from BASF Japan Co., Ltd.) | 20.0 g |
| benzethonium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

| | |
|---|---|
| diclofenac sodium | 0.05 g |
| boric acid | 1.30 g |
| sodium borate | 0.88 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

Comparative Example 2

| | |
|---|---|
| diclofenac sodium | 0.1 g |
| γ-CyD (available from Wacker Chemicals East Asia Co., Ltd.) | 0.7 g |
| boric acid | 1.45 g |
| sodium borate | 0.35 g |
| PVP $_{K25}$ (Kollidon ™ 25: available from BASF Japan Co., Ltd.) | 3.0 g |
| benzethonium chloride | 0.005 g |
| 0.1N HCl/0.1N NaOH amount sufficient for achieving | pH 7.5 |
| purified water | ad. 100 ml |

The same procedures used in Example 1 were repeated except that the foregoing formulation is substituted for that used in Example 1 to give an eye drop.

Comparative Example 3

| | |
|---|---|
| diclofenac sodium | 0.1 g |
| γ-CyD (available from Wacker Chemicals East Asia Co., Ltd.) | 10.0 g |
| boric acid | 1.70 g |
| sodium borate | 0.07 g |
| PVP $_{K25}$ (Kollidon ™ 25: available from BASF Japan Co., Ltd.) | 10.0 g |
| benzethonium chloride | 0.005 g |
| 0.1N HCl/0.1N NaOH amount sufficient for achieving | pH 6.5 |
| purified water | ad. 100 ml |

The same procedures used in Example 1 were repeated except that the foregoing formulation is substituted for that used in Example 1 to give an eye drop.

Comparative Example 4

| | |
|---|---|
| diclofenac sodium | 0.1 g |
| α-CyD (CELDEX ™ : available from Nihon Shokuhin Kako Co., Ltd.) | 5.0 g |
| boric acid | 1.30 g |
| sodium borate | 0.88 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

Comparative Example 5

| | |
|---|---|
| diclofenac sodium | 0.1 g |
| β-CyD (RINGDEX ™ BR: available from Mercian Co., Ltd.) | 1.0 g |
| boric acid | 1.30 g |
| sodium borate | 0.88 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

Comparative Example 6

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| PVP $_{K25}$ (Kollidon ™ 25: available from BASF Japan Co., Ltd.) | 23.0 g |
| benzethonium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

Comparative Example 7

| | |
|---|---|
| diclofenac sodium | 0.1 g |
| γ-CyD (available from Wacker Chemicals East Asia Co., Ltd.) | 3.0 g |
| boric acid | 1.30 g |

-continued

| | |
|---|---|
| sodium borate | 0.88 g |
| PVP $_{K12}$ (Kollidon ™ 12PF: available from BASF Japan Co., Ltd.) | 25.0 g |
| benzethonium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

Comparative Example 8

| | |
|---|---|
| γ-CyD (available from Wacker Chemicals East Asia Co., Ltd.) | 3.0 g |
| boric acid | 1.30 g |
| sodium borate | 0.88 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

Comparative Example 9

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| benzethonium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

Comparative Example 10

| | |
|---|---|
| diclofenac sodium | 0.05 g |
| α-CyD (CELDEX ™: available from Nihon Shokuhin Kako Co., Ltd.) | 1.0 g |
| boric acid | 1.60 g |
| sodium borate | 0.16 g |
| PVP $_{K25}$ (Kollidon ™ 25: available from BASF Japan Co., Ltd.) | 2.0 g |
| 0.1N HCl/0.1N NaOH amount sufficient for achieving | pH 7.0 |
| purified water | ad. 100 ml |

The same procedures used in Example 1 were repeated except that the foregoing formulation is substituted for that used in Example 1 to give an eye drop.

Comparative Example 11

| | |
|---|---|
| diclofenac sodium | 0.05 g |
| β-CyD (RINGDEX ™ BR: available from Mercian Co., Ltd.) | 0.9 g |
| boric acid | 1.60 g |
| sodium borate | 0.16 g |
| PVP $_{K25}$ (Kollidon ™ 25: available from BASF Japan Co., Ltd.) | 2.0 g |
| 0.1N HCl/0.1N NaOH amount sufficient for achieving | pH 7.0 |
| purified water | ad. 100 ml |

The same procedures used in Example 1 were repeated except that the foregoing formulation is substituted for that used in Example 1 to give an eye drop.

Comparative Example 12

| | |
|---|---|
| diclofenac sodium | 0.05 g |
| α-CyD (CELDEX ™: available from Nihon Shokuhin Kako Co., Ltd.) | 1.0 g |
| boric acid | 1.60 g |
| sodium borate | 0.16 g |
| PVP $_{K25}$ (Kollidon ™ 25: available from BASF Japan Co., Ltd.) | 2.0 g |
| sodium edetate | 0.1 g |
| 0.1N HCl/0.1N NaOH amount sufficient for achieving | pH 7.0 |
| purified water | ad. 100 ml |

The same procedures used in Example 1 were repeated except that the foregoing formulation is substituted for that used in Example 1 to give an eye drop.

Comparative Example 13

| | |
|---|---|
| diclofenac sodium | 0.05 g |
| β-CyD (RINGDEX ™ BR: available from Mercian Co., Ltd.) | 0.9 g |
| boric acid | 1.60 g |
| sodium borate | 0.16 g |
| PVP $_{K25}$ (Kollidon ™ 25: available from BASF Japan Co., Ltd.) | 2.0 g |
| sodium edetate | 0.1 g |
| 0.1N HCl/0.1N NaOH amount sufficient for achieving | pH 7.0 |
| purified Water | ad. 100 ml |

The same procedures used in Example 1 were repeated except that the foregoing formulation is substituted for that used in Example 1 to give an eye drop.

Comparative Example 14

| | |
|---|---|
| diclofenac sodium | 0.1 g |
| γ-CyD (available from Wacker Chemicals East Asia Co., Ltd.) | 3.0 g |
| boric acid | 1.45 g |
| sodium borate | 0.35 g |
| hydroxyethyl cellulose (FUJICHEMI HEC ™ CF-G: available from Fuji Chemical Co., Ltd.) | 0.5 g |
| benzethonium chloride | 0.005 g |
| 0.1N HCl/0.1N NaOH amount sufficient for achieving | pH 7.5 |
| purified water | ad. 100 ml |

The same procedures used in Example 1 were repeated except that the foregoing formulation is substituted for that used in Example 1 to give an eye drop.

Comparative Example 15

| | |
|---|---|
| diclofenac sodium | 0.1 g |
| γ-CyD (available from Wacker Chemicals East Asia Co., Ltd.) | 3.0 g |
| boric acid | 1.45 g |

-continued

| | |
|---|---|
| sodium borate | 0.35 g |
| METOLOSE ™ SM400 (available from Shin-Etsu Chemical Co., Ltd.) | 0.5 g |
| benzethonium chloride | 0.005 g |
| 0.1N HCl/0.1N NaOH amount sufficient for achieving | pH 7.5 |
| purified water | ad. 100 ml |

The same procedures used in Example 1 were repeated except that the foregoing formulation is substituted for that used in Example 1 to give an eye drop.

Comparative Example 16

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| PVP $_{K25}$ (Kollidon ™ 25: available from BASF Japan Co., Ltd.) | 3.0 g |
| cetylpyridinium chloride | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

Comparative Example 17

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| PVP $_{K25}$ (Kollidon ™ 25: available from BASF Japan Co., Ltd.) | 3.0 g |
| chlorhexidine gluconate | 0.005 g |
| 0.1N HCl/0.1N NaOH amount sufficient for achieving | pH 8.0 |
| purified water | ad. 100 ml |

The same procedures used in Example 1 were repeated except that the foregoing formulation is substituted for that used in Example 1 to give an eye drop.

Comparative Example 18

| | |
|---|---|
| diclofenac sodium | 0.1 g |
| γ-CyD (available from Wacker Chemicals East Asia Co., Ltd.) | 3.0 g |
| boric acid | 1.30 g |
| sodium borate | 0.88 g |
| PVP $_{K25}$ (Kollidon ™ 25: available from BASF Japan Co., Ltd.) | 3.0 g |
| methylparaben | 0.026 g |
| propylparaben | 0.014 g |
| 0.1N HCl/0.1N NaOH amount sufficient for achieving | pH 8.0 |
| purified water | ad. 100 ml |

To 80 ml of purified water pre-heated to about 60° C., there are added methylparaben and propylparaben and the mixture is sufficiently stirred to dissolve them. After cooling the solution to room temperature, γ-CyD, boric acid, sodium borate, diclofenac sodium and PVP $K_{25}$ are added to the solution to dissolve the same. The pH of the resulting solution is adjusted to 8.0 by the addition of 0.1N HCl or 0.1N NaOH, then purified water is added till the total volume reaches 100 ml, followed by sterilization through filtration to give an eye drop.

The following test examples are given for proving that the ocular irritation caused by diclofenac sodium is alleviated in the pharmaceutical preparation of the present invention.

Test Example 1 [Test for Feeling When Applied to Human Eyes (Ocular Irritation)]

Physiological saline and the pharmaceutical preparations prepared in Examples 1 to 9 and Comparative Examples 1 to 5 each was dropped (one drop each) in the eyes of 10 persons to thus inspect the preparations for the feeling (ocular irritation) observed during the period ranging from the time immediately after the application thereof to 3 minutes after the application. The results thus obtained are summarized in Table 1. In Table 1, the feeling is evaluated according to the following four criteria.

0: no ocular irritation
1: slight smart
2: smart
3: pain or strong smart

TABLE 1

| | Human Feeling (Ocular Irritation) | | | | | | | | | | | |
|---|---|---|---|---|---|---|---|---|---|---|---|---|
| | 1 | 2 | 3 | 4 | 5 | 6 | 7 | 8 | 9 | 10 | Tot. | Av. |
| Physiological Saline | 0 | 0 | 0 | 0 | 0 | 0 | 0 | 0 | 1 | 0 | 1 | 0.1 |
| Example | | | | | | | | | | | | |
| 1 | 0 | 0 | 1 | 0 | 0 | 0 | 0 | 0 | 1 | 0 | 2 | 0.2 |
| 2 | 1 | 0 | 1 | 0 | 0 | 0 | 1 | 0 | 2 | 0 | 5 | 0.5 |
| 3 | 0 | 0 | 1 | 0 | 0 | 0 | 0 | 1 | 1 | 0 | 3 | 0.3 |
| 4 | 0 | 0 | 0 | 0 | 0 | 0 | 0 | 0 | 1 | 0 | 1 | 0.1 |
| 5 | 1 | 0 | 1 | 0 | 0 | 0 | 0 | 0 | 1 | 0 | 3 | 0.3 |
| 6 | 1 | 0 | 1 | 0 | 0 | 1 | 0 | 0 | 1 | 0 | 4 | 0.4 |
| 7 | 1 | 0 | 1 | 0 | 0 | 1 | 0 | 0 | 2 | 0 | 5 | 0.5 |
| 8 | 1 | 0 | 1 | 0 | 0 | 1 | 0 | 0 | 1 | 0 | 4 | 0.4 |
| 9 | 0 | 0 | 1 | 0 | 0 | 0 | 0 | 0 | 1 | 0 | 2 | 0.2 |
| Comparative Ex. | | | | | | | | | | | | |
| 1 | 3 | 3 | 3 | 3 | 3 | 3 | 3 | 3 | 3 | 3 | 30 | 3.0 |

TABLE 1-continued

| | Human Feeling (Ocular Irritation) | | | | | | | | | | | |
|---|---|---|---|---|---|---|---|---|---|---|---|---|
| | 1 | 2 | 3 | 4 | 5 | 6 | 7 | 8 | 9 | 10 | Tot. | Av. |
| 2 | 2 | 1 | 2 | 3 | 2 | 2 | 2 | 3 | 3 | 2 | 22 | 2.2 |
| 3 | 3 | 2 | 3 | 3 | 2 | 2 | 3 | 3 | 3 | 2 | 26 | 2.6 |
| 4 | 3 | 2 | 3 | 3 | 3 | 2 | 3 | 3 | 3 | 2 | 27 | 2.7 |
| 5 | 3 | 2 | 2 | 2 | 2 | 2 | 2 | 3 | 3 | 2 | 23 | 2.3 |

The results shown in Table 1 clearly indicate that the preparations of the present invention have considerably alleviated ocular irritation due to diclofenac sodium and the ocular irritation thereof is almost identical to that observed for physiological saline.

Moreover, the following Test Example is given for proving that the PVP concentration in the preparation of the present invention desirably ranges from 1 to 20%.

Test Example 2 [Test of Feeling When Applied to Human Eyes (stickiness)]

Physiological saline and the pharmaceutical preparations prepared in Examples 10 to 17 and Comparative Examples 6 to 7 each was dropped (one drop each) in the eyes of 10 persons to thus inspect the preparations for the feeling (stickiness) observed during the period ranging from the time immediately after the application thereof to 3 minutes after the application. The results thus obtained are summarized in Table 2. In Table 2, the feeling is evaluated according to the following four criteria.

0: no stickiness or disagreeable feeling
1: slightly sticky, but no disagreeable feeling
2: sticky in some degree and disagreeable in some extent
3: sticky and disagreeable feeling

TABLE 2

| | Human Feeling (Stickiness) | | | | | | | | | | | |
|---|---|---|---|---|---|---|---|---|---|---|---|---|
| | 1 | 2 | 3 | 4 | 5 | 6 | 7 | 8 | 9 | 10 | Tot. | Av. |
| Physiological Saline | 0 | 0 | 1 | 0 | 0 | 0 | 0 | 0 | 1 | 0 | 2 | 0.2 |
| Example | | | | | | | | | | | | |
| 10 | 1 | 1 | 1 | 0 | 1 | 1 | 2 | 0 | 1 | 1 | 9 | 0.9 |
| 11 | 1 | 1 | 1 | 0 | 1 | 0 | 2 | 0 | 1 | 1 | 8 | 0.8 |
| 12 | 1 | 1 | 1 | 1 | 1 | 1 | 2 | 1 | 1 | 1 | 11 | 1.1 |
| 13 | 2 | 1 | 2 | 1 | 1 | 1 | 1 | 1 | 1 | 1 | 12 | 1.2 |
| 14 | 2 | 2 | 1 | 1 | 2 | 1 | 2 | 1 | 1 | 1 | 14 | 1.4 |
| 15 | 2 | 1 | 2 | 1 | 1 | 1 | 2 | 1 | 1 | 1 | 13 | 1.3 |
| 16 | 2 | 1 | 2 | 1 | 2 | 1 | 2 | 1 | 1 | 1 | 14 | 1.4 |
| 17 | 2 | 1 | 2 | 1 | 1 | 1 | 2 | 1 | 2 | 1 | 14 | 1.4 |
| Comparative Ex. | | | | | | | | | | | | |
| 6 | 3 | 3 | 3 | 2 | 2 | 2 | 3 | 1 | 3 | 2 | 24 | 2.4 |
| 7 | 3 | 2 | 2 | 2 | 2 | 2 | 2 | 1 | 2 | 2 | 20 | 2.0 |

The results shown in Table 2 clearly indicate that the pharmaceutical preparation of the present invention does not have stickiness if the concentration of PVP incorporated into the preparation ranges from 1 to 20%.

The following Test Example is given for proving that the pharmaceutical preparation of the present invention is stable under severe conditions and does not generate any insoluble matter.

Test Example 3 (Test for Storage Stability)

The pharmaceutical preparations prepared in Examples 1 to 9 and Comparative Examples 1 and 8 to 18 were filled in glass ampules and stored at 40° C. for one month to examine whether insoluble matter was formed or not. The results obtained are listed in Table 3. In Table 3, the evaluation criteria are as follows:

-: no insoluble matter was observed
*: insoluble matter was observed

Moreover, the pharmaceutical preparations prepared in Examples 1 to 8 were filled in glass ampules and stored at 40° C. for 6 months to determine the rate of the remaining diclofenac sodium. The results obtained are summarized in the following Table 4.

TABLE 3

| Example No. | Insoluble Matter |
|---|---|
| 1 | — |
| 2 | — |
| 3 | — |
| 4 | — |

TABLE 3-continued

| | Insoluble Matter |
|---|---|
| 5 | — |
| 6 | — |
| 7 | — |
| 8 | — |
| 9 | — |

TABLE 3-continued

| Comparative Example No. | Insoluble Matter |
|---|---|
| 1 | — |
| 8 | * |
| 9 | * |
| 10 | * |
| 11 | * |
| 12 | * |
| 13 | * |
| 14 | * |
| 15 | * |
| 16 | * |
| 17 | * |
| 18 | * |

TABLE 4

| Example No. | Rate of Remaining Diclofenac Sodium (%) |
|---|---|
| 1 | 99.8 |
| 2 | 98.2 |
| 3 | 100.3 |
| 4 | 101.1 |
| 5 | 99.6 |
| 6 | 98.2 |
| 7 | 98.0 |
| 8 | 100.1 |

The results listed in Tables 3 and 4 clearly indicate that the pharmaceutical preparation of the present invention is stable even under severe conditions.

Industrial Applicability

According to the present invention, there can be provided a DFNa-containing anti-inflammatory eye drop, which is stable over a long period of time, does not show any ocular irritation and which may comprise DFNa in a wide range of concentration. Such an eye drop can be effective not only in the maintenance of mydriasis and anti-inflammation during ocular surgery of, for instance, cataract, glaucoma, retinal detachment, removal of vitreous body and strabismus, or in the post-operative therapy, but also in the treatment of Behget's disease, endogenous uveitis and inflammatory disease of outer ocular area such as conjunctivitis, keratitis, episcleritis, pinguecula and hordeolum.

We claim:

1. An anti-inflammatory eye drop, comprising:
   (a) 0.05 to 0.7 weight/volume % of diclofenac sodium;
   (b) 1 to 10 weight/volume % of γ-cyclodextrin;
   (c) 1 to 20 weight/volume % of polyvinyl pyrrolidone;
   (d) 0.002 to 0.01 weight/volume % of benzethonium chloride or 0.002 to 0.005 weight/volume % of benzalkonium chloride, and
   (e) water,
   and having a pH value ranging from 7.0 to 8.5, wherein the eye drop is a solution in water.

2. The eye drop of claim 1 wherein the content of diclofenac sodium ranges from 0.1 to 0.5 weight/volume %.

3. The eye drop of claim 1 wherein the content of γ-cyclodextrin ranges from 3 to 10 weight/volume %.

4. The eye drop as set forth in claim 1 wherein the content of the polyvinyl pyrrolidone ranges from 2 to 10 weight/volume %.

5. The eye drop as set forth in claim 1 wherein the pH value ranges from 7.5 to 8.5.

6. The eye drop as set forth in claim 1 wherein the Fikentscher's K-value of the polyvinyl pyrrolidone ranges from 10 to 95.

7. A method of treating an inflamed eye, comprising administering an effective amount of the eye drop of claim 1 to one or both eyes of a patient in need thereof.

8. The eye drop of claim 1, comprising said benzethonium chloride.

9. The eye drop of claim 1, comprising said benzalkonium chloride.

10. The eye drop of claim 1, which contains a buffering agent.

11. The eye drop of claim 1, which consists essentially of said (a), (b), (c), (d) and (e).

12. The eye drop of claim 11, which contains a buffering agent.

* * * * *